United States Patent [19]
Hanigan et al.

[11] Patent Number: 5,854,006
[45] Date of Patent: Dec. 29, 1998

[54] GAMMA-GLUTAMYL TRANSPEPTIDASE-SPECIFIC ANTIBODY, PRODRUGS FOR THE TREATMENT OF GAMMA-GLUTAMYL TRANSPEPTIDASE-EXPRESSING TUMORS, AND METHODS OF ADMINISTRATION THEREOF

[75] Inventors: Marie Hanigan; Timothy MacDonald, both of Charlottesville, Va.

[73] Assignee: The University of Virginia, Charlottesville, Va.

[21] Appl. No.: 825,349

[22] Filed: Mar. 28, 1997

Related U.S. Application Data

[60] Provisional application No. 60/014,375 Mar. 28, 1996.

[51] Int. Cl.⁶ .............................. G01N 33/53; C07K 16/00
[52] U.S. Cl. ....................... 435/7.21; 435/7.1; 530/387.9; 530/388.1; 530/388.26
[58] Field of Search .............................. 424/130.1, 138.1, 424/141.1, 142.1, 146.1, 184.1; 435/7.1, 7.21; 530/300, 326, 387.9, 388.26, 388.8, 389.7, 388.1

[56] References Cited

PUBLICATIONS

Hanigan et al., Immunohistochemical Detection of Gamma–Glutamyl Transpeptidase in Normal Human Tissue, J. Histochem. Cytochem. 44:1101–1108, 1996.

Shiozawa et al., A Monoclonal Antibody against Human Kidney Gamma–Glutamyl Transpeptidase: Preparation, Immunochemical, and Immunohistochemical Characterization, J. Histochem. Cytochem. 37:1053–1061, 1989.

Glass et al., Detection of Conformational Changes in rat kidney Gamma–Glutamyl Transpeptidase by an Antibody against a Synthethic Peptide Belonging to Part of the Reactive Centre of the Enzyme, Biochem. Mol. Biol. Int. 33:505–513, 1994.

Palfreyman et al., Guidelines for the Production of Polypeptide Specific Antisera Using Small Synthetic Oligopeptides as Immunogens, J. Immunological Methods 75:383–393, 1984.

Sakamuro et al., The Primary Structure of Human Gamma–Glutamyl Transpeptidase, Gene 73:1–9, 1988.

Tate et al., Renal Gamma–Glutamyl Transpeptidases: Structural and Immunological Studies, Arch. Biochem. Biophys. 262:397–408, 1988.

*Primary Examiner*—Patricia Duffy
*Attorney, Agent, or Firm*—Oblon, Spivak, McClelland, Maier & Neustadt, P.C.

[57] ABSTRACT

An antibody is provided which binds to active GGT, and can identify tissues which express GGT on their surface. Many solid tumors express GGT on their surface. Individuals identified with such tumors may be treated with inactivated prodrugs of chemotherapeutic agents at local dosage levels substantially above the maximum dosage levels currently permitted due to side effect limitations. The prodrugs are comprised of chemotherapeutic agents rendered inactive by the attachment of a gamma-glutamyl group thereto. The gamma-glutamyl group is cleaved by GGT on the surface of solid tumor cells expressing GGT, and thus active only locally against the tumor. Side effects are suppressed. The antibody is used to identify solid tumors that are candidates for this treatment, as well as to identify tissues which express GGT and which must therefore be the basis of selection criteria of various available chemotherapeutic agents.

4 Claims, 6 Drawing Sheets

R = H; Doxorubicin
R = Glutamyl; v-glutamyl-doxorubicin

R = H; 9-Aminocamptothecin
R = Glutamyl; v-glutamyl-9-aminocamptothecin

R = H; Hydroxyurea
R = Glutamyl; v-glutamyl-hydroxyurea

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Cys Asp Thr Thr His Pro Ile Ser Tyr Tyr Lys Pro Glu Phe Tyr Thr
 1               5                  10                 15
Pro Asp Asp Gly Gly
            20
```

GAMMA-GLUTAMYL TRANSPEPTIDASE-SPECIFIC ANTIBODY, PRODRUGS FOR THE TREATMENT OF GAMMA-GLUTAMYL TRANSPEPTIDASE-EXPRESSING TUMORS, AND METHODS OF ADMINISTRATION THEREOF

The United States Government may have rights in this application pursuant to Contracts NIHR01CA57530 and P30CA4457906F1.

This application is a regular National application claiming priority from Provisional Application, U.S. application Ser. No. 60/014,375 filed Mar. 28, 1996.

BACKGROUND OF THE INVENTION

Field of the Invention

This invention pertains to antibodies specific for Gamma-Glutamyl Transpeptidase (GGT), inactive prodrugs useful in the treatment of GGT-expressing tumors, and methods of administration of the same. Specifically, a peptide-specific antibody is provided which provides for assays for the detection of GGT expression in solid tumors. Such tumors can be targeted and treated by administration of novel prodrugs which are activated by GGT on the surface of the tumor to be treated. The inactive prodrug is non-toxic, permitting simultaneous elevation of local dosage, with reduced side-effects.

Background of the Prior Art

It is widely acknowledged that many chemotherapeutic regimens fail because the side-effects of the drugs used limit the dose that can be administered. This is particularly true of solid tumors. The clinically tolerated doses are often insufficient to kill all of the cells, thereby enriching the tumor population for drug resistant mutants. Among the surviving tumor cells in below-effective treatment regimens are mutant cells that arise spontaneously within the tumor cell population, and are resistant to the treatment drug. Each subsequent round of chemotherapy enriches the population for the resistant cells, which grow and continue to mutate, some to even higher levels of resistance. There is an established linear-log relationship between dose and tumor kill. The higher the dose of the drug, the greater the chance of eradicating the tumor. While methods have been developed to selectively target and kill tumor cells, many of the targeting methods either reduce the effectiveness of the drug, call for a complex series of reactions to prepare a drug, etc.

In the consideration of solid tumors, it should be recognized that local effective dosage, and systemic dosage, need not be the same. Thus, the only effective portion of the chemotherapeutic agent administered is that which reaches the tumor cell. Many chemotherapeutic agents are administered systemically, however, and only a limited portion of the dosage administered actually reaches the cell. Thus, dose limitations frequently result in only a fraction of the permitted dosage actually reaching the cell. The term local dosage is used herein to describe that dosage which actually reaches the targeted tumor cell population.

It is has been recognized that many human tumors express high levels of GGT. Hanigan et al., Cancer Res. 54:286–290 (1994) and Dempo et al., Oncodevelop. Biol. Medicine 2:21–37 (1981). GGT is a cell surface glycoprotein that cleaves glutathione, glutathione-conjugates and other gamma-glutamyl compounds. Hanigan et al., Carcinogenesis 6:165–172 (1985) and Lieberman et al., Am. J. Pathol. 147:1175–1185 (1995). The function of GGT is most clearly defined in the kidney. GGT is present on the luminal surface of the proximal tubule cells where it cleaves glutathione and glutathione-conjugates in the glomerular filtrate. Curthoys et al., Enzyme 24:383–403 (1979). Glutathione cannot be taken up intact by most cells. GGT cleaves the gamma-glutamyl bond of glutathione releasing glutamic acid and cysteinyl-glycine (CG). CG that can then be hydrolyzed by dipeptidases and the three amino acids reabsorbed. Hanigan et al., Biochemistry 32:6302–6306 (1993). This is the first step in the conversion of such compounds to mercapturic acids.

Studies have demonstrated that induction of GGT is one of the earliest markers of preneoplastic liver cells. Goldsworthy et al., CRC Critical Reviews in Toxicology 17:61–89 (1986). GGT can provide a selective growth advantage to tumor cells by cleaving serum glutathione and thereby providing cells with a secondary source of cysteine. Hanigan et al., Carcinogenesis, supra. It has been postulated that GGT may be critical to the effectiveness of chemotherapeutic agents by effecting the intracellular glutathione levels and by initiating the further metabolism of glutathione-conjugated drugs. Ahmad et al., J. Cell Physiology 131:240–246 (1987) and Hanigan et al., Cancer Research 54:5925–5929 (1994).

Accurate assessments of the presence and amount of GGT expression in human tissues has been difficult however. One assay of choice employs antibodies, which are conventionally used in immunoblotting assays such as Western Blot Technology, and the like. Because the tissue of particular focus is solid tumor tissue, the antibody should preferably be susceptible of use in immunohistochemical staining assays.

The provision of an antibody that detects GGT is not straight forward. The antibody must meet several criteria. The antibody must detect GGT in formalin-fixed sections of human tissues. The antibody must be directed against the peptide backbone of the protein because post-translational modification of GGT, such as glycosylation and addition of sialic acid differs between normal and neoplastic tissue. Yamaguchi et al., Pancreas 4:406–417 (1989) and Arai et al., Clin. Chim. Acta. 210:35–36 (1992). Further, the antibody should not detect the inactive form of GGT encoded by the alternately spliced form of human GGT MRNA that has been detected in the liver, kidney, brain, intestine, stomach, placenta and mammary gland tissues. Pawlack et al., J. Biol. Chem. 265:3256–3262 (1990).

The difficulties encountered in detecting GGT in neoplasmas have also been hampered by a lack of comprehensive analysis of distribution of GGT in normal human tissues. Many human tissues have never been analyzed for GOT expression. There are conflicting results regarding the localization and level of GGT expression in many tissues. Goldbarg et al., Arch. Biochem. Biophys. 91:61–70 (1960), Glenner et al., J. Histochem. Cytochem. 10:481–489 (1962), Albert et al., Acta. Histochem. 18:78–89 (1964) and Shiozawa et al., J. Histochem. Cytochem. 37:1053–1061 (1989).

Accordingly, it remains an object of those of skill in the art to be able to determine the presence of GGT expression in human tumor cells, and, if detected, to advantageously employ the expression of GGT in effecting high local doses of chemotherapeutic agents without toxicity or severe side effects.

The dose limiting side effects of a wide variety of chemotherapeutic agents have been well documented. Among the most promising chemotherapeutic agents, and those in use, are doxorubicin, bleomycin, hydroxyurea, 9-aminocamptothecin and amonafide. Doxorubicin side-effects include cardiomyopathy and myelosuppression as well as nausea and vomiting. Chabner et al., Clinical Pharmacology of Cancer Chemotherapy, in Cancer: Principles and Practice of Oncology, 156–197 (Lippincott 1982). Treatment with bleomycin induces subacute or chronic pneumonitis that progresses to interstitial fibrosis which can be fatal, Id. Hydroxyurea is toxic to the bone marrow. Id. 9-aminocamptothecin can cause neutropenia, nausea and vomiting. Dahut et al., J. Clin. Oncol. 14:1236–1244 (1996). Amonafide, currently in clinical trials, has been reported to cause mylosuppression, vomiting and venous irritation at the infusion sight. Levitt et al., J. Neuro-Onc. 23:87–93 (1995) and Marshall et al., Am. J. Clin. Oncol. 17:514–515 (1994). These side effects limit the systemic dosage that may be administered. The local dosage experienced by the tumor cells is a small fragment of the limited systemic dosage, giving rise to the repeated cycle of survival and resistance described above.

Accordingly, it remains an object of those of ordinary skill in the art to find a way to provide higher local dosages of these side effect dose-limited chemotherapeutic agents, and other agents similarly dosage-limited.

SUMMARY OF THE INVENTION

The above objects, and other objects elaborated more fully below, are met, in part, by the provision of a peptide-specific antibody, GGT 129, that meets the aforementioned criteria for GGT expression detection. The antibody is directed against a peptide of the c-terminus of the heavy subunit of GGT. The 20 amino-acid peptide has the sequence CDTTHPISYYKPEFYTPDDGG (SEQ. ID. NO:1), employing the conventional 1-letter code for amino acids. The peptide, when conjugated to KLH by incubating 0.5 mg peptide and 1.0 mg KLH in 100 mm sodium phosphate buffer, pH 7.4, with 0.2% glutaraldehyde for four hours at room temperature is obtained when the incubation mixture is dialyzed against PBS. Antibodies to the KLH-conjugated peptide can be obtained through conventional measures, e.g., immunizing host organisms, such as rabbits or mice, with the conjugated peptide, recovering the serum therefrom, and isolating the antibody.

The antibody is specific for the peptide. This is the first known antibody specific for a peptide within human GGT. As noted above, GGT is subject to abundant glycosylation and sialic acid residues that are variable. If an antibody is raised against purified GGT, lack of staining may be due to failure to bind due to random variations, rather than the absence of GGT. Additionally, the inactive form expressed by many tissues may be bound by an antibody prepared against the purified GGT, since the inactive form (a truncated form) contains most of the heavy subunits. The identified peptide is not found in the inactive or truncated form, avoiding false positives.

Detection of positive expression of GGT in tumor tissues of potential patients permits treatment of the tumors with altered chemotherapeutic agents. Specifically, agents, such as those discussed above and others, are modified to be inactive as administered. The agents are modified by binding a gamma-glutamyl group at a site rendering the drug inactive. The inactive prodrug travels through the bloodstream in the inactive form, which is non-toxic, until it encounters GGT-positive tumor cells. The GGT expressed on the surface of the cells cleaves the gamma-glutamyl inactivating group, releasing the active form of the drug, achieving a high local dosage, while avoiding dose-limiting side effects. Although many normal tissues express GGT it is localized to the luminal surface of ducts and tubules where it would not be able to activate prodrugs in the serum or in the intestitial fluid. Chemotherapeutic agents should be selected to avoid requirements of activation by the liver, or other tissues distant from the tumor, and should not have significant kidney toxicity, since, as noted above, GGT is expressed in the kidneys.

As GGT has been confirmed to be expressed on the surface of the cells of a wide variety of tumors, and many chemotherapeutic agents are susceptible to inactivation by gamma-glutamyl attachment, to provide a form non-toxic to the patient, the invention makes many tumors amenable to new chemotherapeutic strategies not hampered by low dose limits to avoid side effects.

DESCRIPTION OF THE FIGURES

This invention may be further understood by reference to the figures submitted herewith, summarized in the descriptions set forth below.

DETAILED DESCRIPTION OF THE INVENTION

Figure 1:
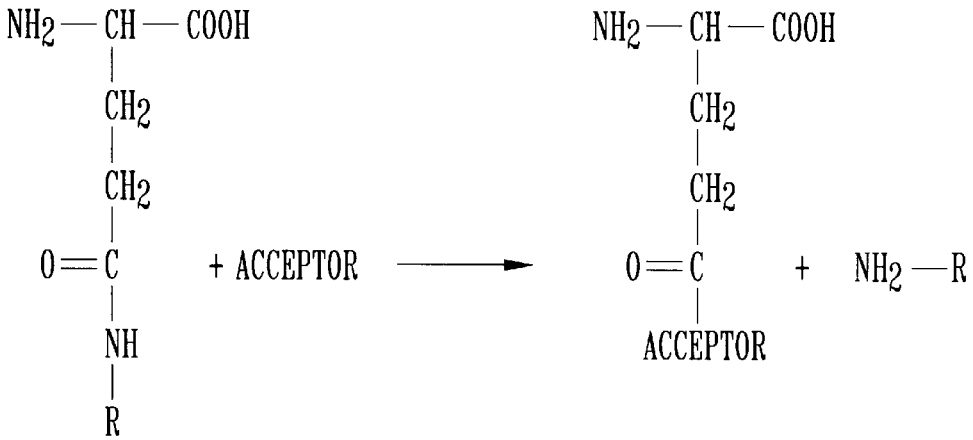
FIG. 1 schematically illustrates the reactions catalyzed by GGT. The Group R designates any chemical group. The acceptor can be any number of amino acids, peptides or water.

This invention includes the peptide-specific antibody for detection of GGT expression in tumor cells and other tissues, assays employing that antibody, GGT-inactivated chemotherapeutic agents, their activation by GGT on the surface of target cells, and methods of administration of these agents to treat specific tumor conditions. While each aspect is described, below, discretely, and may be used separately, the invention provides a complete regimen for the assessment of general tumor types, assay of specific individuals for tumor GGT expression, and treatment of the same. Accordingly, although separate provisions are described separately, below, each is considered part of a greater whole.

GGT-SPECIFIC ANTIBODY

The antibody of the invention, designated GGT129, is prepared against a 20 amino-acid sequence specific to the c-terminus of the heavy subunit of human GGT. The peptide sequence is CDTTHPISYYKPEFYTPDDGG (SEQ. ID. NO:1). This peptide was synthesized with an N-terminal cysteine using conventional technology. The synthesized peptide was conjugated with keyhole limpet hemocyanin (KLH) using conventional technology. Antibodies to the KLH-conjugated peptide were prepared in New Zealand white rabbits, using conventional technology.

The antibody was obtained through affinity purification. Peptide-specific antibody was purified from the serum of the immunized animals by affinity column chromatography. The peptide was linked, via the sulfhydryl group on cysteine to Sulfolink® gel from (Pierce, Rockford, Ill.). A second affinity column was prepared with the peptide and Affi-Gel 15 (Bio-Rad, Richmond, Calif.). After application of the serum obtained from the hosts, columns were rinsed with PBS containing 0.5M NaCl. High-affinity antibody was eluted from both columns by lowering the pH to 2.8. Affinity-purified antibody was dialyzed vs. PBS and stored at −80° C. in 1% BSA. Both columns yielded purified antibody effective for immunohistochemical staining.

Samples of normal human myometrium, intestinal epithelium and endometrium were obtained from surgical specimens, Department of Pathology, University of Virginia Health Sciences Center. Human liver and kidney were obtained from autopsy material. Tissue was stored at −80° C. Tissue was homogenized with a Potter-Elvehjem homogenizer in PBS at 4° C. The protein concentration in the homogenate was determined by BCA protein assay (Pierce).

Washed human sperm were obtained from the Human Gametes and Embryo Laboratory, University of Virginia Health Sciences Center. Sperm were washed free of seminal fluid by pelleting through a two-step Percoll gradient (47.5 and 90% Percoll) then washed with Biggers Whitten and Whittingham medium (Irvine Scientific, Irvine, Calif.) containing 5 mg/ml human serum albumin.

GGT activity in the tissue homogenates and washed human sperm was quantified according to the method of Tateishi et al., Gann. 67:215–222 (1976). Glycylglycine 40 mM was used as an acceptor. One unit of GGT activity is defined as the amount of enzyme that releases 1 $\mu$mol p-nitroaniline per minute at 25° C. Tissue homogenates were diluted to 0.5 mg/ml in 125 mM Tris, pH 6.8, 1% SDS, 5% $\beta$-mercaptoethanol, 10% glycerol and were boiled for 2 minutes. Samples (1 $\mu$gram per lane) were electrophoresed on 5–20% polyacrylamide-SDS gel and electroblotted to nitrocellulose (0.45 $\mu$pore) (Schleicher and Schuell, Keene, N.H.). The blots were blocked overnight at 4° C. in 10 mM Tris, pH 8.0, 150 mM NaCl, 0.05% Tween 20 (TBST) containing 5% bovine serum albumin. Blots were rinsed in TBST, and incubated for 2 hours at room temperature in affinity-purified GGT129 diluted 1:20,000 relative to the serum concentration. Blots were washed in three changes of TBST and incubated for 2 hours with peroxidase-conjugated goat anti-rabbit IgG diluted 1:10,000 in TBST. After a fmal rinse in TBST, immunolabeled bands were visualized by enhanced chemiluminescence (BM cherniluminescence wester blotting reagents) (Boehringer Mannheim, Indianapolis, Ind.).

5 $\mu$m sections from routine zinc formalin-fixed, paraffin-embedded normal tissues were obtained from archival autopsy and surgical pathology blocks at the University of Virginia Health Sciences Center. For immunohistochemical staining, paraffin was removed and the tissue rehydrated with four 10-minute incubations in xylene, three 5-minute incubations in 100% ethanol, three 5-minute incubations in 95% ethanol and a 5-minute wash in distilled water. Endogenous peroxidase activity was inhibited by two 15-minute incubations in 0.3% $H_2O_2$ in methanol, followed by two 5-minute washes in PBS. Endogenous biotin was blocked with a 15-minute incubation in avidin blocking solution (Avidin/Biotin block kit) (Vector Laboratories, Burlingane, Calif.). A 3-minute wash in PBS, a 15-minute incubation in biotin blocking solution and a 10-minute wash in PBS. Slides were incubated for 10 minutes in PBS containing 1.5% normal goat serum (Gibco) (Grand Island, N.Y.). Affinity-purified GGT129 antibody in 1% BSA was diluted in 1.5% goat serum-PBS. The primary antibody was diluted 1:1,000 relative to the starting serum concentration. Slides were incubated for 45 minutes in primary antibody. Control sides were incubated in an equivalently diluted solution of 1% bovine serum albumin. The antibody was removed and slides were washed for 3 minutes in PBS. The slides were incubated with biotinylated anti-rabbit IgG and avidin-linked peroxidase (Vectastain Elite ABC peroxidase kit) (Vector). Peroxidase was localized with the Biogenex liquid DAB substrate (Biogenex, San Ramon, Calif.). Slides were incubated for 3 minutes in 0.5% cupric sulfate to fix the stain, rinsed in deionized water and counterstained for 3 minutes in Gills Hematoxylin. All incubations were done at room temperature. After rinsing, the slides were dehydrated with 95% and 100% ethanol and xylene, then cover slipped with Permount. A section of normal human kidney was included as a positive control with each section stained.

Sperm were assayed for GGT activity by the biochemical assay described above. In addition, washed sperm were smeared on a glass slide, air-dried and stained histochemically for GGT activity as previously described in Hanigan et al., (1994) supra.

Western blot analysis of whole tissue homogenates was used to determine the specificity of the GGT129 antibody. GGT was analyzed in human myometrium, intestinal epithelium, endometrium, liver, and kidney. Biochemical assay of GGT activity in the homogenates showed that myometrium had less than 1 U GGT activity/g protein, intestinal epithelium, 3.6±0.4 U/g protein, endometrium 7.0±0.3 U/g protein, liver 20.7±0.9 U/g protein, and kidney 103±2.0 U/g protein. The homogenates were subjected to SDS-PAGE electrophoresis, blotted, and stained with the GGT129 antibody. A single band at approximately 66 KD, corresponding to the heavy subunit of human GGT, was reactive with the antibody. Among the tissues analyzed, the relative level of GGT activity corresponded to the amount of the heavy subunit detected on the Wester blot.

Immunohistochemical staining with the anti-GGT polyclonal antibody revealed that GGT was restricted to specific cell types (Table 1). The majority of GGT-positive cells were epithelial. In addition, macrophages in many tissues were immunoreactive. Fat and muscle were consistently GGT-negative. Fibrous stroma was generally negative for GGT, but thin bands of immunopositive fibroblasts were seen in some sections of bladder, colon, liver, breast, and ovary.

Concordant with the high levels of GGT activity measured by the biochemical assay, immunohistochemical staining revealed intense positivity of renal proximal tubule cells with localization to the luminal surface. The glomeruli and distal tubules were negative. The transitional epithelium of the bladder and the ureter was negative for GGT. As noted above, in some sections the stroma under the transitional epithelium was positive for GGT.

Major and minor salivary gland epithelium showed strong immunohistochemical staining, with localization to the apical surface of salivary ducts. The acini were negative. Bronchial and lung epithelium lacked GGT staining. Alveolar macrophages were weakly GGT-positive. Esophageal squamous epithelium was negative, but duct cells draining the submucosal glands were positive. Analysis of the stomach showed no staining of the surface epithelium, but weak apical staining was observed in some of the antral mucous glands. The duodenum and small intestine had weak positive apical staining of the crypts and very weak positive staining on the intestinal surface. Crypts and epithelium in the colon and appendix were negative. Goblet cells lacked immunoreactivity. Macrophages within the appendix were positive.

In the liver, GGT was localized to the bile canaliculi of the hepatocytes. The staining was most intense in the hepatocytes near the portal areas. The luminal surface of biliary epithelium in both the small and the large ducts was also positive. The apical surface of the gallbladder epithelium was moderately stained. In the pancreas, the acinar cells were strongly positive and apical staining of the duct epithelium was present. Islet cells were completely negative.

In the brain and spinal cord, the endothelial cells lining the capillaries showed striking GGT-positivity. The endothelial cells lining arteries were negative, although weak staining was present in the perivascular cells surrounding large arteries. Neurons and glial cells were negative.

Many cells within the male reproductive system showed high levels of GGT immunostaining. In the testis, the Sertoli cells had strong apical membrane immunoreactivity and Leydig cells were moderately positive. An undescended testicle devoid of germ cells was stained for GGT to highlight the Sertoli cells, which stained strongly positive. The epithelium lining the epididymis, seminal vesicle, and vas deferens showed high levels of GGT on the apical surface. The luminal surface of the glandular epithelium in the prostate was GGT-positive, although the underlying basal epithelial cells were negative. GGT was present in seminal fluid, making it difficult to ascertain whether germ cells were GGT-positive. Therefore, human sperm washed free of seminal fluid were stained histochemically and assayed biochemically for GGT activity. Sperm were negative for GGT activity with both methods.

TABLE I

Immunobissochemical detection of GGT in normal human tissues

| Tissue | Immunopositive cells |
| --- | --- |
| Urinary system | |
| Kidney | Proximal tubule cells |
| Bladder | Stroma under transitional epithelium (focal) |
| Respiratory system | |
| Bronchus | Salivary ducts |
| Lung | Alveolar macrophages (weak) |
| Digestive tract | |
| Salivary gland | Salivary ducts |
| Stomach | Antral mucous glands (focal, weak) |
| Duodenum and ileum | Crypts and lining epithelium (very weak) |
| Colon | Stromal cells (focal) |
| Appendix | Macrophages |
| Liver | Bile ducts and canaliculi |
| Gallbladder | Surface of epithelium |
| Pancreas | Acinar cells and ducts |
| Reproductive system | |
| Testis | Sertoli cells and Leydig cells |
| Epididymis | Epithelium and secretions |

TABLE I-continued

Immunobissochemical detection of GGT in normal human tissues

| Tissue | Immunopositive cells |
| --- | --- |
| Seminal vesicle | Epithelium |
| Vas | Epithelium |
| Prostate | Epithelium and secretions |
| Ovary | Leydig cells (weak) |
| | Stromal cells (focal, weak) |
| Fallopian tubes | Nonciliated epithelium (moderate to weak) and cilia on ciliated epithelium |
| Endometrium | Secretory and proliferative phase epithelium and secretions |
| Cervix | Endocervical glands and secretions |
| Breast | Ducts and ductules |
| Immune System | |
| Spleen | Connective tissue around arterioles |
| Lymph nodes | Macrophages |
| Endrocrine Glands | |
| Adrenal | Capillary endothelium cortical cells (weak) |
| Parathyroid | Capillary endothelium |
| Thryroid | Follicular epithelium (weak) |
| Nervous system | |
| Brain and spinal cord | Capillary endothelium |
| Other | |
| Skin | Sweat glands (eccrine) |
| Placenta | Amnion and chorion |
| Umbilical cord | Amnionic cells |
| Fetus | |
| Kidney | Proximal tubules |
| Intestine | Epithelium |
| Liver | Bile canaliculi |
| Pancreas | Ducts |
| Adrenal cortex | Cortical epithelium |

The female reproductive tract had less intense GGT-positivity than the male system. Germ cells, surface epithelium, and most stromal cells in the ovary were negative. Leydig cells showed a very weak level of staining. Occasionally, a small group of spindle-shaped stromal cells within the ovary was GGT-positive. The cilia on the epithelium of the Fallopian tubes stained positive, and nonciliated epithelium was weakly stained. Within the uterus there was amixture of GGT-positive and -negative glands in both the secretory and the proliferative phase of the menstrual cycle. The fluid within the GGT-positive secretory glands was also GGT-positive. Uterine smooth muscle was negative. The squamous epithelium of the cervix was negative, whereas the endocervical glands and their luminal secretions had moderate staining intensity at the surface. Breast tissue showed variable apical staining of the epithelium of the ducts and ductules. Secretions within the positive ductules were also GGT-positive.

Squamous and sebaceous epithelia of the skin, skeletal muscle, cardiac muscle, fat, nerves, and blood vessels were all GGT-negative. Sweat glands (eccrine) showed apical immunostaining. In the spleen, some of the connective tissue around arterioles and within the stroma showed GGT-positive staining. Splenic lymphocytes and those within lymph nodes were negative. However, tingible body macrophages and other histiocytes within lymph nodes were immunoreactive.

In the adrenal gland, the capillary endothelial cells were positive for GGT. The adrenal cortical cells were very weakly immunopositive, unlike the adrenal medullary cells, which were negative. Follicular epithelial cells in the thyroid showed GGT staining, whereas the colloid did not show GGT activity. Staining of parathyrod epithelium was negative.

Placental and fetal tissues were also analyzed for GGT immunoreactivity. Trophoblasts and chorionic villi were negative, whereas cells in the chorionic layer and amnion were moderately GGT-positive. Expression of GGT in fetal tissue was similar to that in adult tissue. In a 12-week-old fetus, the tissue that expressed GGT included proximal tubules in the kidney, bile canaliculi of the hepatocytes, ducts within the pancreas, and the apical surface of the intestinal epithelium. The adrenal cortex was weakly positive. Tissues that did not express GGT included hematopoietic elements within the liver, skeletal muscle, and cartilage. Gestational endometrium was also positive.

Following the above methods, irnmunostaining of a variety of human tumors, for expression of GGT, has been conducted. The results of GGT expression testing of human tumors is summarized in Table II.

TABLE II

Expression of GGT in Human Tumors

| Histologic Classification | # GGT-Positive Tumors Total # of Tumors Analyzed |
|---|---|
| Carcinomas | |
| Breast | 61/83 |
| Prostate | 70/71 |
| Ovarian (Epithelial) | 16/22 |
| Adrenal | 0/3 |
| Hepatocellular | 11/12 |
| Renal | 6/7 |
| Intestinal | 6/10 |
| Pancreaticobiliary | 10/11 |
| Endometrial | 7/12 |
| Basal Cell | 0/9 |
| Squamous Cell | 3/13 |
| Urethral | 2/3 |
| Extramammary Paget's | 3/6 |
| Salivary | 3/10 |
| Gastric | 3/9 |
| Thyroid | 21/22 |
| Lung | 22/24 |
| Embryonal | 2/2 |
| Other | |
| Pleural Mesotheliomas | 0/10 |
| Lymphomas | 0/21 |
| Sarcomas | 7/55 |

The results of the GGT testing set forth above contain important implications for determining GGT-mediated chemotherapy, as discussed below. GGT is expressed on the brush border of the renal proximal tubule cells. Any drug that is excreted in the urine that would be activated by GGT would be present in the kidneys. Accordingly, drugs having pronounced renal toxicity are not promising candidates for the GGT-mediated chemotherapy discussed below.

GGT is also expressed on the luminal surface of epithelium lining glandular tissues. This includes sweat glands, salivary glands, hepatic bile canaliculi, pancreatic acini, mammary duct, prostate glands and endocervical glands. GGT is restricted to the luminal surface of these cells. Due to the localization of the enzyme in these tissues, it is unlikely that GGT would be in contact with prodrugs transported by the blood. Prodrugs taken up by the glandular cells and excreted into the lumen might be activated to the active form by GGT. Accordingly, chemotherapeutic agents that would be toxic to these epithelia would not make preferred candidates.

GGT is also expressed by the endothelial cells lining the brain capillaries. GGT prodrugs transported in the blood are not activated by GGT in the brain, however. Misicka et al., Life Sciences 58:905–911 (1996). GGT activation appears to occur only when the prodrug would be injected intrathecally.

GGT is also expressed at low levels on some peripheral blood mononuclear cells. The blasts, which are killed by many chemotherapeutic drugs, are GGT-negative. The GGT level of activity on peripheral blood mononuclear cells is sufficiently low as to be unlikely to activate a prodrug inactivated by gamma-glutamyl linkage.

GGT is also elevated in the serum of patients with impaired liver function, due to pathological conditions such as cirrhosis, gallstones and the like. The use of GGT-mediated prodrugs in patients with elevated serum levels of GGT would not provide for enhanced local dosages.

Additional detailed discussion of human tissue GGT expression, as reflected in Tables I and II, and the assays set forth above, can be found in Hannigan et al., J. Histochem. Cytochem. 44:1101–1108 (1996) which is not prior art with respect to this application, and is incorporated herein by reference. To the extent specific tissues strongly express GGT on their surface, or would otherwise uptake GGT-mediated prodrugs, selection of chemotherapeutic agent so as to be nontoxic to critical tissues is important.

The immunolocalization studies summarized in Table II demonstrate that there is heterogeneity among tumors with regard to GGT expression. Prostate tumors were most consistently GGT-positive, and high percentages of both breast and epithelial ovarian tumors were also GGT-positive. This heterogeneity indicates that in each patient to be treated, the tumor to be treated will have to be stained for GGT expression in order to determine which patients would benefit from treatment with the GGT-mediated prodrugs discussed below. It should be noted that many of the tumors with consistent GGT expression are poorly differentiated. The neoplastic cells do not form glandular structures. The lack of polarization in the tumor cells results in GGT being distributed over the entire cell surface. As a result, the GGT on these tumor cells would be in contact with the prodrugs coming into the cell from the blood. Cleavage of the prodrug would provide a high local concentration of the active parent compound desired. Poorly differentiated tumors often present at a high stage and generally do not respond well to standard doses, in particular side effect-limited doses, of chemotherapeutic drugs. These tumors are likely to be the ones to most benefit from GGT-mediated prodrugs discussed below.

GGT-MEDIATED PRODRUGS

To increase local dosage without inducing side effects, conventional agents will be modified by derivatizing these chemotherapeutic compounds with proven activity against solid tumors. This strategy is applicable to a wide range of structurally diverse compounds. Five compounds are representative: 9-aminocamptothecin, a topoisomerase I inhibitor; bleomycin, which produces DNA strand breaks; hydroxyurea, an inhibitor of ribonucleotide synthesis; amonafide, a topoisomerase II inhibitor; and doxorubicin, an anthracycline with antitumor activity. None of these compounds requires activation by the liver and none have significant kidney toxicity. Each can be derivatized to a gamma-glutamyl prodrug that may be inactive as a toxin. This invention should not be understood to be limited to these agents.

Figure 2A:
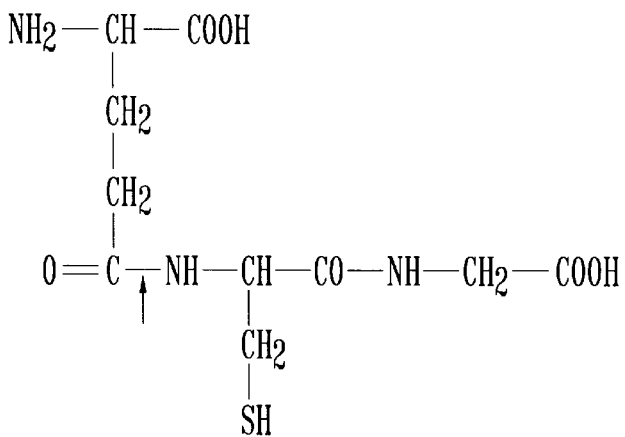
FIGS. 2A–2C provide structural representation of 3GGT substrates. Substrates 2A, 2B and 2C are, respectively, glutathione, gamma-glutamyl-p-nitroanilide and leukotriene $C_4$. GGT cleaves the substrates at the gamma-glutamyl bound, designated by an arrow. The only specificity of the structural diverse compounds that serve as substrates for GGT is the gamma-glutamyl-amide linkage.
Figure 2B:
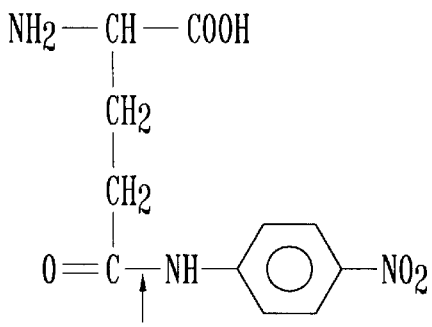
Figure 2C:
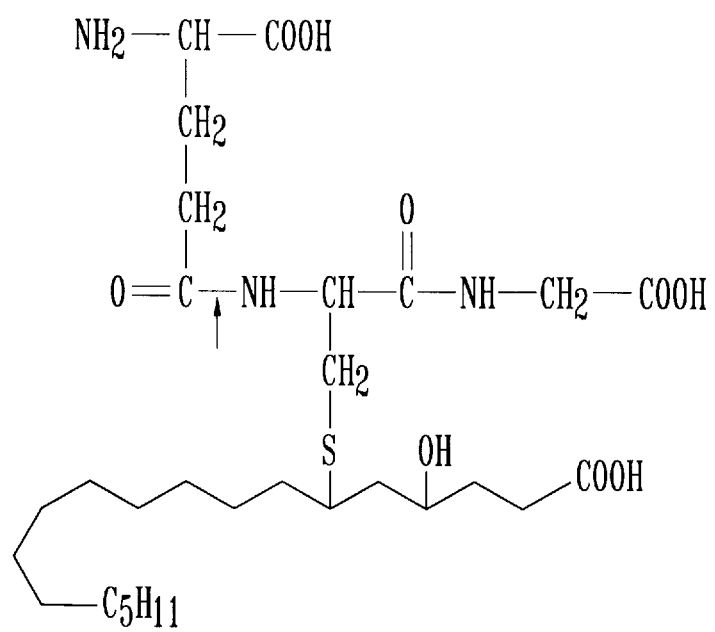

GGT is a cell surface enzyme. A general formula for the reaction catalyzed by GGT is shown in FIG. 1. It cleaves gamma-glutamyl amide bonds, and can transfer the gamma-glutamyl group to a primary amine on free amino acids or peptide acceptors. The enzyme can also use water as an acceptor resulting in the hydrolysis of the substrate. Glutathione and glutathione conjugated compounds are the most common physiologic substrates for the enzyme. However, as shown in FIG. 2, GGT can utilize a wide variety of gamma-glutamyl compounds as substrates. GGT can cleave gamma-glutamyl derivatives of a diverse group of drugs. The only specificity in the structure of the substrate is that it contain a free glutamic acid linked via the carboxy-terminus of the side chain to an amine group. GGT does not transport substrates or products across the cell membrane. Gamma-glutamyl prodrugs of this invention are designed to be inactive until GGT cleaves the gamma-glutamyl group thereby liberating the active parent compound.

Synthesis of Gamma-Glutamyl Amonafide

Amonafide is a topoisomerase II inhibitor that is currently in phase II clinical trials. Amonafide gamma-glutamyl prodrug has been synthesized. It serves as a prototype to demonstrate the principle that addition of a gamma-glutamyl group can stabilize a drug in an inactive form and the gamma-glutamyl derivative can be activated by GGT-positive cells.

The protocol for synthesis of the drug is as follows: N,N-Dimethylethylenediamine (8.22 mmol) was added dropwise to a suspension of 3-nitro-1,8-naphthalic anhydride (4.11 mmol) in ethanol (20 ml). The dark solution was refluxed for 4 hr. The solvent was evaporated off and the crude product, mitonafide, was purified by column chromatography eluting with methanol in chloroform (1:9). $SnCl_2.H_2O$ (3.51 mmol) and $H_2O$ (0.125 $\mu$l) were added to a solution of mitonafide (0.702 mmol) in ethanol (5 ml). The solution was refluxed until the reaction was completed (1,5 h) as analyzed by analytical thin-layer chromatography (TLC). TLC was carried out on precoated aluminum backed silica gel 60F-254 plates (Merck) and were visualized with phosphomolybdic acid/ethanol solution. The solution was cooled to room temperature and poured onto ice. The pH was neutralized to pH 7–8 with $NaHCO_3$ powder, and the aqueous layer was extracted with ethyl acetate (3×10 ml). The organic layers were combined, dried over $Na_2SO_4$ and filtered. The solvent was removed under reduced pressure yielding the product as a bright yellow solid (100%) and was used without further purification. $^1H$ NMR spectra of the amonafide were obtained with a General Electric QE300 spectrometer at 300 MHz. All chemical shifts are recorded in ppm. Elemental analyses were performed in The Department of Chemistry on a Perkin-Elmer PE 2400 C,H,N analyzer. 1H NMR (300 MHz, $CDCl_3$) $\delta$ 8.22 (d, J=7.5 Hz, 1H), 7.90 (s, 1H), 7.83 (d, J=8.4 Hz, 1H), 7.50 (t, J=8.1 Hz, 1H), 4.23 (t, J=6.6 Hz, 2H), 4.08 (bs, 2H), 2.60 (t, J=6.6 Hz, 2H), 2.30 (s, 6H).

Figure 3:
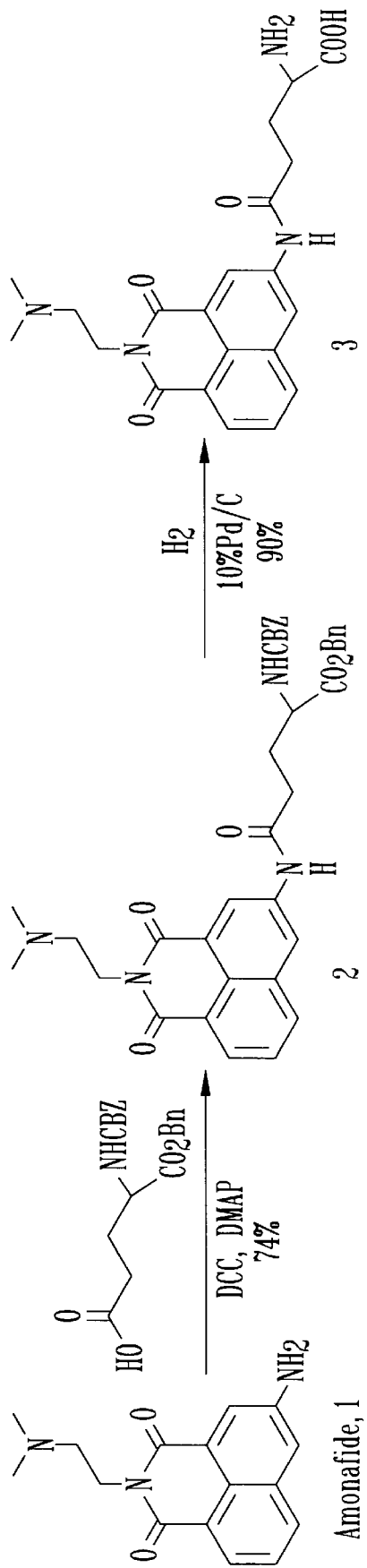
FIG. 3 is a schematic illustration of the synthesis of gamma-glutamyl amonafide.

A solution containing (0.265 mmol) of amonafide derivative 3 (FIG. 3) and (0.53 mmol) N-Carbobenzyloxy-D-glutamic acid-$\alpha$-benzyl ester in $CH_2Cl_2$ (2 ml) was cooled to 0° C. Dicyclohexylcarbodiimide (0.53 mmol) and a catalytic amount Dimethylaminopyridine (10 mol%) was added and the solution was stirred overnight. The urea was filtered off, the filtrate was concentrated under reduced pressure and purified by column chromatography eluting with methanol in chloroform (1:9) to yield N-Carbobenzyloxy-$\alpha$-Benzyl ester-D-Glutamyl-$\gamma$-amonafide (74%). $^1H$ NMR (300 MHz), $CDCl_3$) $\delta$ 9.0 (bs, 1H), 8.74 (bs, 1H), 8.40 (d, J=7.2 Hz, 1H), 8.21 (s, 1H), 8.01 (d, J=8.4 Hz, 1H) 7.64 (t, J=7.2 Hz, 1H), 7.34 (bm, 10H), 5.83 (d, J=7.2 Hz, 1H), 5.19 (d, J=3 Hz, 2H), 5.15 (s, 2H), 4.55 (m, 1H), 4.33 (t, J=6 Hz, 2H), 2.75, (m, 2H), 2.52 (m, 2H), 2.41 (s, 6H), 2.38 (m, 2H).

The protected glutamyl-amonafide 3 (0.188 mmol) was dissolved in ethanol (5 ml) and a catalytic amount of 10% Pd/C was added. The solution was stirred under $H_2$ (1 atmosphere) for 48 h. The suspension was filtered through a Celite plug and the solvent was evaporated off under reduced pressure. The product, gamma-glutamyl-amonafide, was recrystallized in methanol/acetone and isolated as yellow brown crystals (90%). $^1H$ NMR (300 MHz, $CD_3OD$) $\delta$ 8.62 (s, 1H), 8.55 (s, 1H), 8.37 (d, J=7.5 Hz, 1H), 8.17 (s, J=7.5 Hz, 1H), 7.67 (t, J=7.2 Hz, 1H), 4.40 (t, J=6 Hz, 2H), 3.78 (m, 1H), 3.41 (t, J=5.4 Hz, 2H), 3.15 (s, 6H), 2.63 (m, 2H), 2.14 (m, 2H).8

The synthetic approach for the other agents follows the methodology developed for gamma-glutamyl amonafide. The desired amine-containing drug is coupled with $\alpha$-benzyl N-carbobenzoxy-glutamate to generate the bis-benzyl protected gamma-linked glutamyl prodrug through carbodiimide-mediated ester activation protocols. The protected prodrug may then be deprotected via hydrogenolysis to yield the free gamma-glutamyl prodrug. With the exception of hydroxyurea, each of the parent drugs is known to be stable to these chemical transformations.

Synthesis of Gamma-Glutamyl 9-Aminocamptothecin:

9-Aminocamptothecin is a DNA toposiomerase I inhibitor currently undergoing clinical evaluation. The drug exhibits low aqueous solubility and its activity can be profoundly attenuated by the binding to human serum albumin of the ring-opened hydroxy carboxylate, which is produced by hydrolysis of the lactone and appears to be in equilibrium with the parent. The basis for this observation appears to be that the selective binding (>200:1) of the carboxylate to albumin shifts the equilibrium toward the acid. Thus, development of a water soluble prodrug with low serum albumin binding affinity capable of localized release may have significant implications for the chemotherapy of GGT expressing tumors. In particular, epithelial ovarian carcinoma appears to be responsive to DNA topoisomerase I inhibitors. Gamma-glutamyl 9-aminocamptothecin may enable significant dose escalation in the treatment of this disease, since upon GGT-mediated release of the parent drug from the inactive prodrug, the parent drug should be locally absorbed or systemically inactivated by association with serum albumin.

The chemistry of camptothecin has been extensively investigated with a full range of synthetic manipulations undertaken. The chemistry for the development of gamma-glutamyl 9-aminocamptothecin is well precedented.

Synthesis of Gamma-Glutamyl Bleomycin:

The bleomycins are a family of glycopeptide antibiotics that exhibit potent cytotoxic activities. The activity of the bleomycins is thought to be a consequence of DNA damage mediated through oxygen free radical species produced by the iron-complexed antibiotic. Although complex, the molecule has been synthesized and extensive synthetic manipulation of the bleomycin framework has been conducted. The bleomycin structures vary primarily in the terminal, intercalation segment of the molecule, as illustrated by the $A_2$ and $B_2$ structures illustrated in FIG. 4. For the bleomycin systems that do not possess guanidine side chains (e.g., bleomycin $A_2$), acylation can occur at multiple sites with the primary amino groups of the $\beta$-aminoalanyl and the 4-aminopyrazone moieties exhibiting the greatest nucleophilicities. Regiochemically selective amino acylation can occur through modulation of the conditions and the presence of metal ions. Thus, either amino or both primary amine groups may undergo gamma-glutamylation with slight modification of the reaction conditions for the aminoacylation protocol.

Synthesis of Gamma-Glutamyl Doxorubicin

Doxorubicin is a DNA topoisomerase II-directed agent, that additionally exhibits redox activity. The drug has undergone extensive structure-activity studies in efforts to optimize the therapeutic index. These studies have included the development of a range of N-acyl derivatives which are currently under clinical evaluation. The N-acyl derivatives exhibit intrinisically lower DNA topoisomerase I inhibitory activity. Moreover, since anthracycline intercalation appears to be the initial step in the formation of the drug-DNA-enzyme complex, the incorporation of the amino acid side chain into the anthracycline framework would be anticipated to additionally depress intercalation and hence topoisomerase II-mediated activity. The synthetic entries into the N-acylated doxorubicin species are analogous to the methodology above; hydrogenolysis of benzyl-protecting groups appended to the anthracycline skeleton has been previously undertaken. Thus, precedent for the synthesis of gamma-glutamyl doxorubicin is available.

Synthetic Approach to Gamma-Glutamyl Hydroxyurea

Gamma-glutamyl hydroxyurea cannot be synthesized by the route outlined above, becasue the hydroxyl moiety of hydroxyurea is more reactive in acylation reactions and because the molecule is sensitive to reduction under the hydrogenolysis procedure. A number of N'-acyl hydroxyurea derivatives are known and one, caracemide (N-acetyl-N-(methylcarbamoyloxy)-N'-methylurea; NSC 253272), has undergone clinical evaluation as an antitumor agent. The target for this agent appears to be similar to that of hydroxyurea, although the mechanism of enzyme inactivation may be distinct and occur through transacylation processes. However, caracemide, a triacylamine derivative, exhibits lability in aqueous solutions hydrolyzing to the diacylamine derivative, which may be a substrate for subsequent deacylation. Thus, caracemide may be a prodrug, either hydrolyzing directly or enzymatically releasing the species acive in the inhibition of ribonucleotide reductase.

Figure 5:
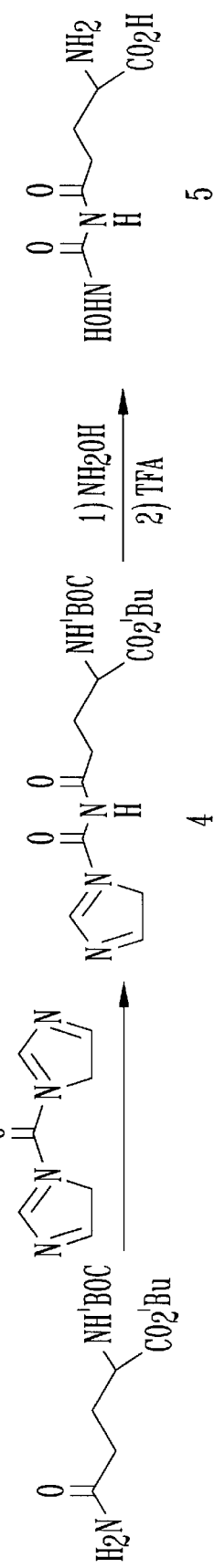
FIG. 5 is a schematic representation of the synthesis of gamma-glutamyl hydroxyurea.
Figure 4A:
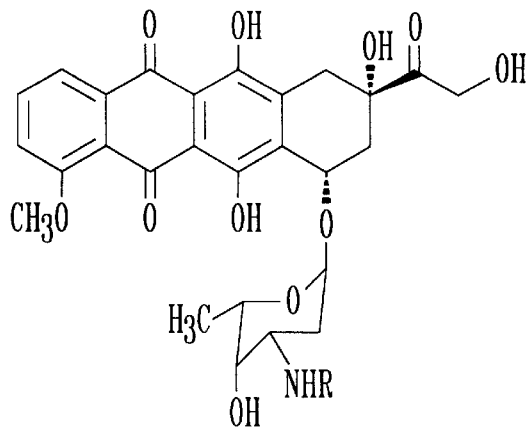
FIG. 4 provides structural illustrations of chemotherapeutic drugs and their corresponding gamma-glutamyl prodrug derivatives of the claimed invention.
Figure 4B:
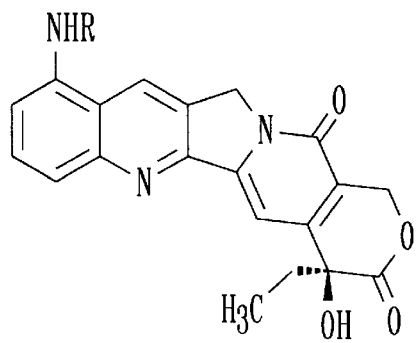
Figure 4C:
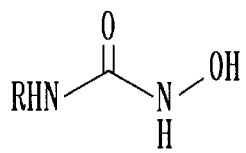
Figure 4D:
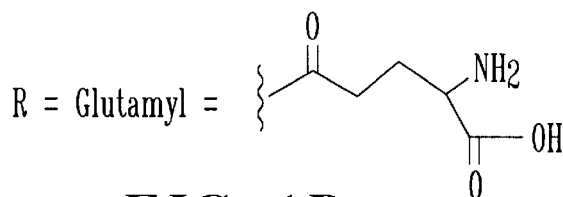
Figure 4E:
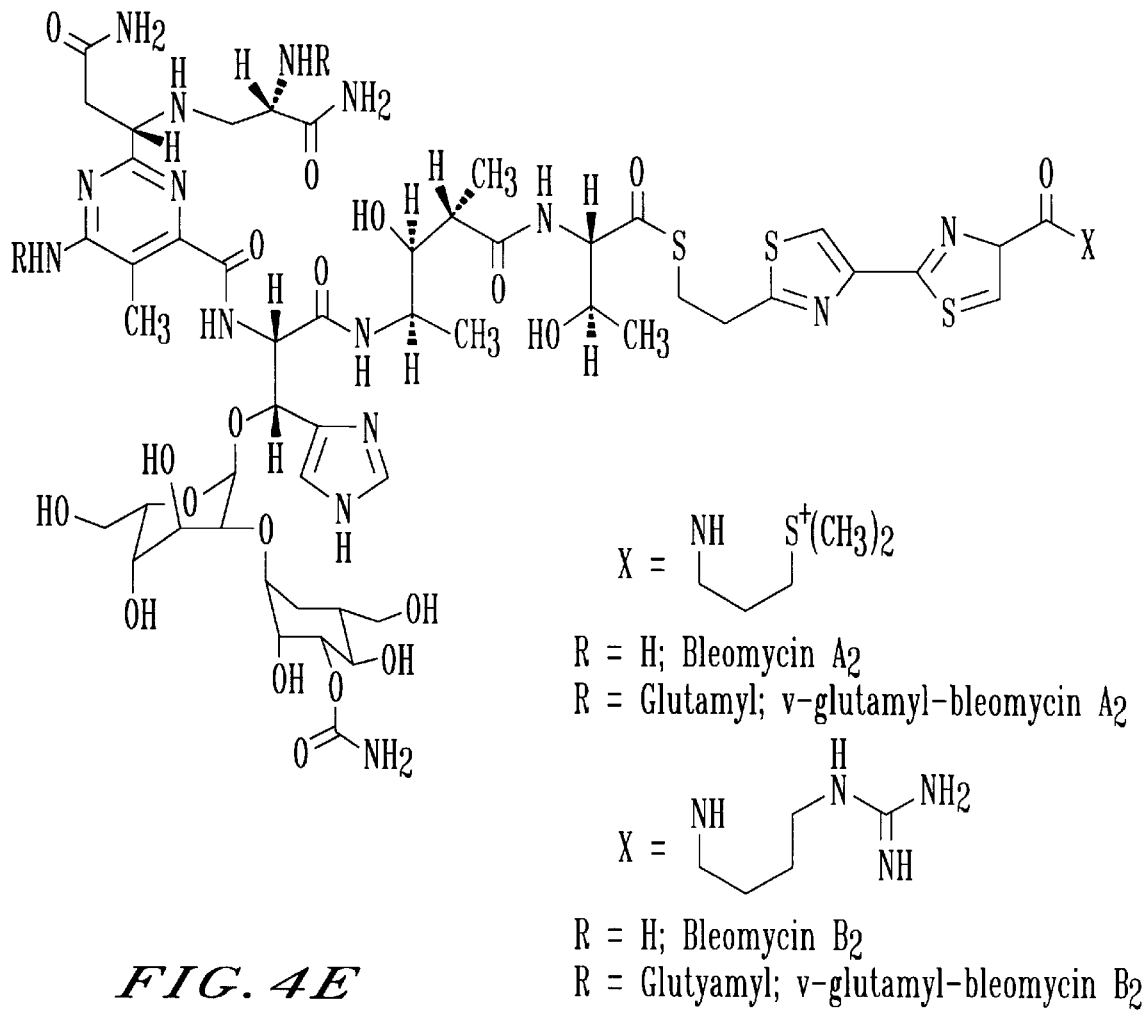

The synthetic route outlined for the preparation of gamma-glutamyl hydroxyurea is illustrated in FIG. 5. The synthesis proceeds by aminoacylation of tertiary-butyl N-BOC-glutaminate with carbonyl diimidazole, followed by treatment with hydroxylamine.

ANTITUMOR ACTIVITY

The prodrugs of this invention may be tested for activity against tumors assayed positively for GGT expression by both in vitro and in vivo testing. Actual testing, and testing protocols, are set forth below. These are not exclusive, and other testing protocols known to those of skill in the art may be employed.

Initially gamma-glutamyl prodrugs are tested in vitro for toxicity toward GGT-positive and GGT-negative tumors. Performing these experiments in a controlled manner requires cell lines that differ only in their expression of GGT. three human tumor cell lines will be used: PC3 cells, a human prostate tumor cell line, SK-OV-3 a human ovarian tumor cell line and MDA-MB-231, a human breast cancer cell line. These three cell lines which do not express GGT may be transfected with a plasmid containing cDNA for human GGT. The prodrug is tested for toxicity in both the GGT-positive and GGT-negative cells from each line. Data on the toxicity of gamma-glutamyl amonafide in GGT-positive and GGT-negative PC3 cells is presented below. These in vitro tests also provide information on the solublity and stability of the gamma-glutamyl prodrugs.

Gamma-glutamyl prodrugs may also be tested for activity against tumors formed in nude mice from the GGT-positive and GGT-negative cell lines. With the in vitro and in vivo testing gamma-glutamyl prodrugs that are as efective as the parent compound in killing GGT-positive tumors, but are not toxic to GGT-negative cells as determined by their inability to kill GGT-negative tumors may be identified.

GGT-Positive and GGT-Negative Human Tumor Cell Lines

Three human tumor cell lines have been chosen for these studies: the PC3 cell line, a human prostate cell line established from a bone metastasis of a prostatic adenocarcinoma, SK-OV-3 a human ovarian tumor cell line and MDA-MD-231 a human breast cancer cell line. We obtained the PC3 cell line (ATCC CRL 1434) from the American Type Culture Collection (Rockville, Md.). PC3 cells were tested for expression of GGT by both biochemical and histochemical assays and found to be GGT-negative. The SK-OV-3 cell line (ATCC HBT 77) and MDA-MD-231 cell line (ATCC HTB 26) may be obtained from ATCC as well. Both of these cell lines are reported to be GGT-negative.

GGT-positive PC3 cell lines and GGT-negative control cell lines were constructed with GGT/pLEN-PT, an expression vector containing a full length cDNA clone for GGT. This same transfection vector was used to transfect NIH/3T3 cells and Hepa 1–6 cells. We use the same vector and transfection strategy to obtain GGT-positive SK-OV-3 cells and MDA-MD-231 cells. Briefly, the transfection is done using the calcium phosphate transfection kit from Stratagene (LaJolla, Calif.). Five×$10^5$ cells are transfected with 10 $\mu$g of pLEN/GGT plus 2 $\mu$g of pWLneo, a transfection vector that contains a G418 resistance marker. Control cells are transfected with pWLneo alone. Stable transformants are selected by the addition of G418 to the culture medium. Independent colonies of G418 cells are picked and grown into cell lines. Cell lines are characterized histochemically and biochemically for GGT expression.

Toxicity Testing in vitro

The gamma-glutamyl prodrug and the parent drug are tested for toxicity toward GGT-positive and GGT-negative cells. The cells are plated in 96-well dishes, allowed to attach and grow for several days. Test compounds are dissolved in culture medium. The test protocols include experiments in which the cells are exposed to the drugs continuously for 3 days and experiments in which the cells are exposed to the drugs for 3 hours then the drugs removed and fresh medium added back to the cells. Three days after the beginning of the drug exposure the number of viable cells is determined by the MTT assay. Briefly, the MTT assay is a calorimetric assay in which the tetrazolium salt, 3-(4,5-dimethylthiazol-2-yl)-2,5-diphenyl tetrazolium bromide (MTT) is converted to the colored product formazan by dehydrogenase activity in living cells. The assay provides a quantitative measure of the number of viable cells per well and can be read on a multiwell scanning spectrophotometer. Each 96-well plate can be used to test 24 solutions, each in triplicate plus a blank well without cells to determine background absorbence. With the MTT assay multiple dilutions of the parent drug and gamma-glutamyl prodrug can be rapidly assayed for toxicity. The in vitro experiments include dose response curves and analysis of the time course of toxicity. Cultures containing mixtures of GGT-positive and GGT-negative cells are used to test the toxicity of the prodrugs and parent compounds. Since GGT is on the surface of the cell it cleaves the prodrug extracellularly. While applicants do not wish to be bound by this theory once the drug is activated it enters and kills adjacent GGT-negative tumor cells as well as the GGT-positive tumor cells. This is important, because many GGT-positive clinical tumors contain a mixture of GGT-positive and GGT-negative cells. In order to destroy the entire tumor the activated prodrugs would have to kill the GGT-negative cells surrounding the GGT-positive tumor cells.

GGT-Positive and GGT-Negative Tumors in Nude Mice

PC3 cells form tumors when injected into nude mice. There is an extensive literature on the development of PC3 tumors in nude mice because PC3 tumors have been used to test the therapeutic activity of experimental chemotherapy drugs. Both SK-OV-3 and MDA-MD-231 cells also form tumors in nude mice and can be used to test the therapeutic effect of chemotherapy drugs in vivo.

Athymic nu/nu mice may be obtained from Takonic Farm (New York, N.Y.). Athymic nu/nu mice are housed in isolation boxes supplied with Hepa-filtered, forced air and acidified water. Cages, bedding and food are autoclaved prior to use. All surgical procedures including injection of tumor cells are performed in a sterile laminar flow hood (BSL2 cabinet, Class II type A/BE).

For experiments with the PC3 cells, $10^6$ GGT-positive PC3 cells or $10^6$ GGT-negative PC3 cells are dispersed in a 1:1 dilution of matrigel (Collaborative Research Inc.) at 4° C. and injected subcutaneously into 6-week old athymic nu/nu mice. This protocol results in the formation of visible tumors at 100% of the injection sites in 2 to 3 weeks. Seventy-two animals are injected, 36 with GGT-positive PC3 cells and 36 with GGT-negative PC3 cells. After measurable tumors have arisen, 12 of the animals in each group may be treated with the parent compound, 12 with the gamma-glutamyl prodrug and 12 serve as untreated controls. The parent compound and the gamma-glutamyl prodrug are administered at equimolar doses. The doses are derived from previously published in vivo studies of the parent compound in mouse tumor model systems. The drugs should be injected interperitoneally. Intravenous injections in mice are technically difficult and generally inconsistent. None of the surfaces lining the peritoneum are GGT-positive so the gamma-glutamyl prodrugs should be absorbed into the blood stream intact. Tumor size is measured weekly with slide calipers. Tumor growth is monitored following treatment. Animals are weighed weekly. Throughout the experiment animals are observed daily. If animals become moribund, cachectic or unable to obtain food or water they are euthanized. The length of the experiment is dependent on the rate of growth of the tumors and the response of the tumors to treatment. Based on related studies with cisplatin the experiments may conclude 2 to 3 months after the beginning of treatment. At the conclusion of the experiment tumors are excised, weighed and processed for immunochemical and histologic analysis.

Histochemical and Histologic Analysis of Tumors from Nude Mice

At the time the animals are sacrificed the tumors are removed and fixed in Bouin's fixative. To ensure that the tumors retain their GGT-positive and GGT-negative phenotype one-third of the tumors in each group of animals is immunostained with the rabbit polyclonal antibody GGT129. (Note that the cells were transfected with the cDNA for human GGT). The fixed tissue is embedded in paraffin, sectioned at 4 µm. The tumors are immunostained. The immunostaining procedure will be the same one used to stain the clinical tumors.

In vitro Toxicity of Amonafide and Gamma-Glutamyl Amonafide toward GGT-Positive and GGT-Negative PC3 Cells Amonafide and the prodrug derivative gamma-glutamyl amonafide were tested for toxicity towards GGT-positive and GGT-negative prostate tumor cells. The results demonstrate that the parent compound was equally toxic to both GGT-positive and GGT-negative cells. Addition of the gamma-glutamyl group inactivated the drug so that it was no longer toxic to GGT-negative cells. Gamma-glutamyl amonafide was activated by and was toxic to the GGT-positive cells.

GGT-Positive and GGT-Negative PC3 Cells

The PC3 cell line (ATCC CRL 1434) is a human prostate tumor cell line established from a bone metastasis of a prostatic adenocarcinoma. PC3 cells obtained from ATCC were tested for expression of GGT with biochemical and histochemical assays and fond to be GGT-negative. The GGT-positive PC3 cells and control PC3 cells transfected with the selectable antibiotic resistance marker were maintained in RPMI 1640 media (BRL/GIIBCO Laboratories, Grand Island, N.Y.), with 10% fetal bovine serum (HyClone Laboratories, Logan, Utah) and penicillin-streptomycin (BRL/GIBCO Laboratories, Grand Island, N.Y.).

Toxicity Assay

The toxicity of the amonafide and gamma-glutamyl amonafide towards GGT-positive and GGT-negative PC3 cells was assessed with the MTT assay. GGT-negative and GGT positive cells were plated in 96-well dishes. The cells attached and grew for several days. Test compounds were dissolved in RPMI-1640 medium. Cells were exposed to the drugs for 3 hours, after which the drugs were removed and replaced with RPMI 1640 medium containing 10% fetal bovine serum and penicillin-streptomycin. Three days after the drug exposure the number of viable cells was determined by the MTT assay.

Results of Toxicity Assays

Figure 6B:
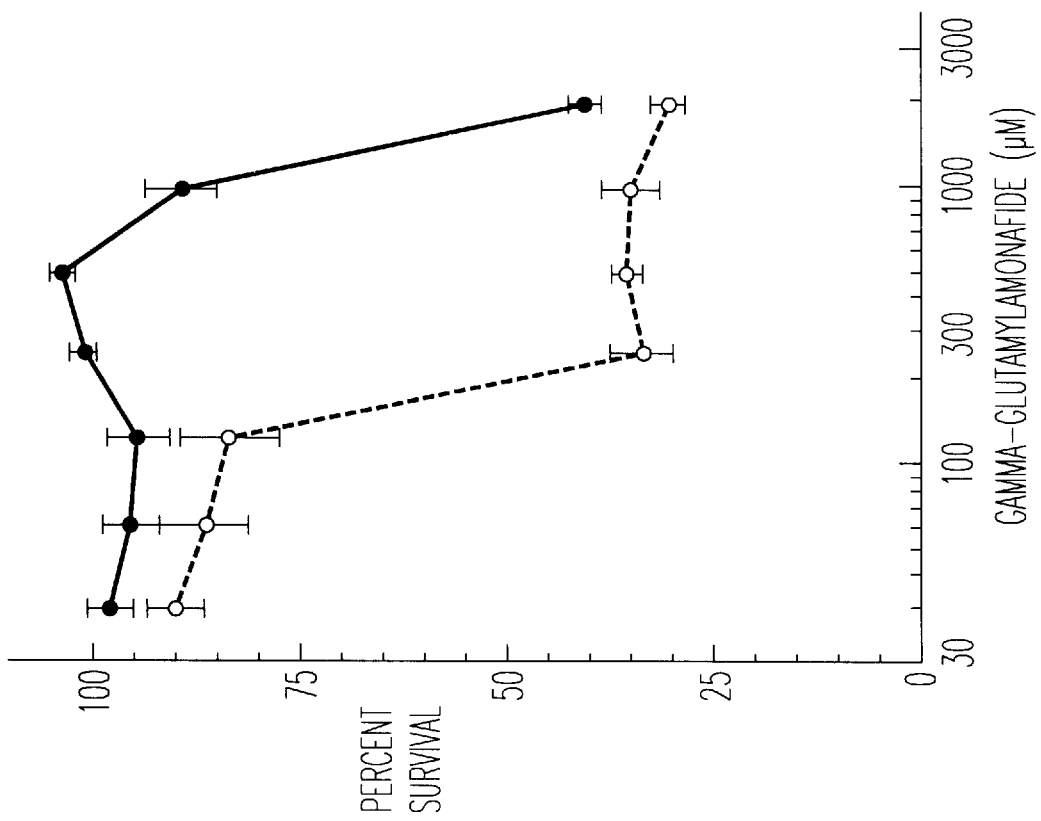
FIGS. 6A and 6B are a graphic illustration of the results of in vitro toxicity testing of a amonafide and gamma-glutamyl amonafided on GGT-positive and GGT-negative PC3 cells. GGT-positive results are designated by open circles and GGT-negative results are designated by closed circles.
Figure 6A:
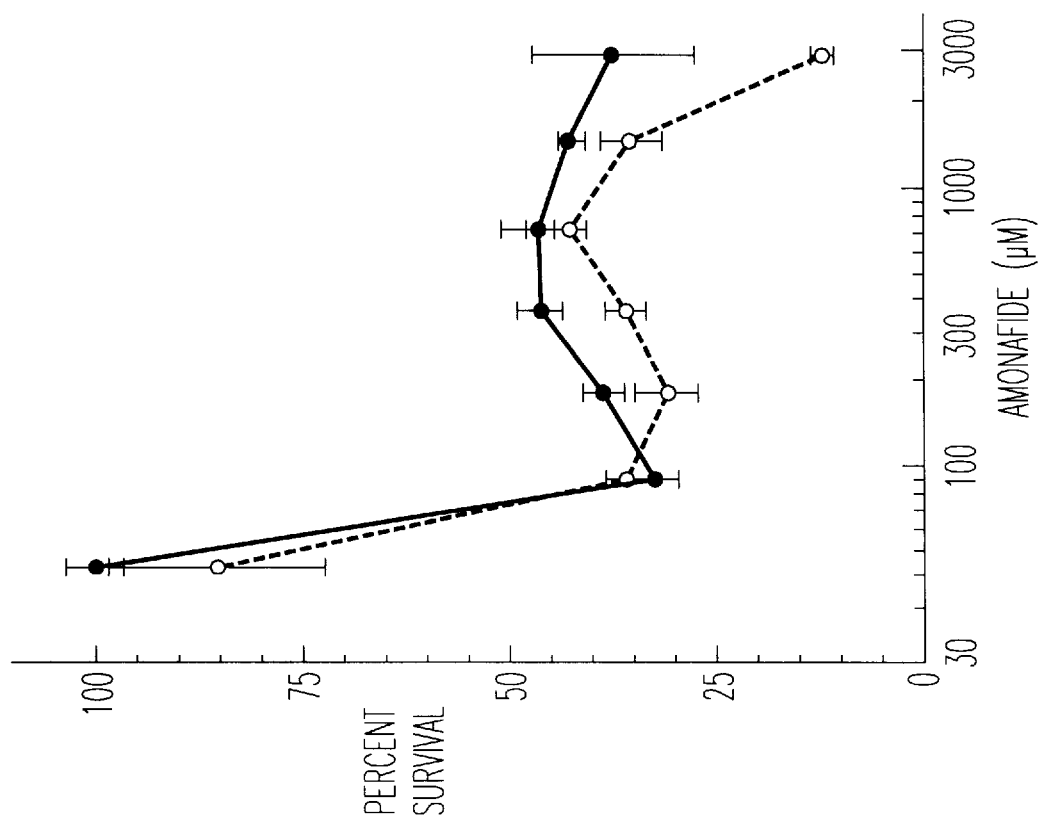

The results of our experiments with amonafide and gamma-glutamyl amonafide show that a three hour exposure to the parent compound, amonafide, was equally toxic to both the GGT-positive and GGT-negative PC3 cells. However, the gamma-glutamyl derivative was 10-fold more toxic to the GGT-positive cells than the GGT-negative cells. These data clearly demonstrate that GGT-positive cells can activate the prodrug. FIG. 6. It is unclear why very high concentrations of the gamma-glutamyl prodrug was toxic to the GGT-negative cells. One possible explanation is that a low level of parent drug was present as a contaminant in the preparation of the gamma-glutamyl amonafide.

The above invention, including the GGT129 antibody, five specific prodrugs, methods of administration and the like have been described in terms of generic expressions, and by specific example and embodiment. Examples and embodiments set forth are not limiting, except where so indicated. In particular, other chemotherapeutic agents, selected according to the guidelines set forth above, will occur to those of ordinary skill in the art for inactivation by gamma-glutamyl attachment, and may be effectively used in this invention. Dosages will vary, from patient to patient, and prodrug to prodrug. The in vitro and in vivo testing programs set forth above will allow those of ordinary skill in the art to empirically establish acceptable dosage levels. As dosage levels for the parent compounds of the prodrugs disclosed and claimed herein have already been established in the art, these are a starting point from which higher levels that may be tolerated can be calculated. Further, the antibody described has been obtained through methods specifically set forth and disclosed. Other antibodies, having identical or similar binding affinity and specificity for GGT can be obtained through identical or similar methods. The preparation of these similar antibodies does not involve inventive skill, and such antibodies remain within the scope of the invention. In particular, derivatives of the peptide for which the antibody is specific, as well as other conjugation agents to generate an immunogenic response will occur to those of skill in the art, without the exercise of inventive faculty. The invention is not so limited, unless expressly restricted by the claims set forth below.

What is claimed as new and desired to be secured by Letters Patent of the United States is:

1. A method of assaying a tissue culture sample for the presence of gamma-glutamyl transpeptidase (GGT) expression, comprising combining an isolated antibody specific for a peptide having SEQ. ID. NO:1 with said tissue sample under conditions which permit antibody binding, and inspecting said sample to determine whether binding of said antibody has occurred, wherein any such binding is indicative of the presence of GGT expressing tissue.

2. An isolated antibody which binds specifically to a polypeptide having SEQ. ID. NO:1.

3. An isolated antibody produced by immunization of a mammal with a composition comprised of a polypeptide having SEQ. ID. NO:1, said polypeptide being conjugated to keyhole limpet hemocyanin, wherein said conjugate, when injected into a mammal, induces an immune response in the mammal to produce antibodies which bind specifically to said polypeptide.

4. An isolated antibody which binds specifically to the peptide backbone of the active form of gamma-glutamyl transpeptidase (GGT), wherein said antibody does not specifically bind to the inactive form of GGT encoded by alternately spliced human MRNA of liver, kidney, brain, intestine, stomach, placenta and mammary gland tissues.

* * * * *

UNITED STATES PATENT AND TRADEMARK OFFICE
Certificate

Patent No. 5,854,006

Patented: December 29, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Marie Hanigan, Charlottesville, VA (US).

Signed and Sealed this Sixteenth Day of January 2007.

WILLIAM R. DIXON, JR.
*Special Program Examiner*
Technology Center 1600

UNITED STATES PATENT AND TRADEMARK OFFICE
Certificate

Patent No. 5,854,006                                                                                               Patented: December 29, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Marie Hanigan, Charlottesville, VA (US).

Signed and Sealed this Sixteenth Day of December 2008.

ROBERT B. MONDESI
                                                                                              *Supervisory Patent Examiner*
                                                                                                      Art Unit 1645